(12) United States Patent
Birk (10) Patent No.: US 7,811,298 B2
(45) Date of Patent: Oct. 12, 2010

(54) FATIGUE-RESISTANT GASTRIC BANDING DEVICE

(75) Inventor: Janel Birk, Oxnard, CA (US)

(73) Assignee: Allergan, Inc., Irvine, CA (US)

( * ) Notice: Subject to any disclaimer, the term of this patent is extended or adjusted under 35 U.S.C. 154(b) by 486 days.

(21) Appl. No.: 10/492,784

(22) PCT Filed: Aug. 26, 2003

(86) PCT No.: PCT/US03/26678

§ 371 (c)(1),
(2), (4) Date: Apr. 18, 2005

(87) PCT Pub. No.: WO2004/019671

PCT Pub. Date: Mar. 11, 2004

(65) Prior Publication Data

US 2005/0192531 A1    Sep. 1, 2005

Related U.S. Application Data

(60) Provisional application No. 60/407,219, filed on Aug. 28, 2002.

(51) Int. Cl.
   *A61B 17/08*    (2006.01)
   *A61F 2/02*     (2006.01)
(52) U.S. Cl. .............................. 606/157; 600/31; 600/37
(58) Field of Classification Search ................. 606/151, 606/153, 157, 158, 201, 202; 600/29–31, 600/37, 207; 128/898
See application file for complete search history.

(56) References Cited

U.S. PATENT DOCUMENTS

| 1,174,814 A | 3/1916 | Brennan et al. |
| 3,840,018 A | 10/1974 | Heifetz |
| 4,118,805 A | 10/1978 | Reimels |
| 4,399,809 A * | 8/1983 | Baro et al. ..................... 600/31 |
| 4,408,597 A * | 10/1983 | Tenney, Jr. .................. 600/31 |
| 4,558,699 A | 12/1985 | Bashour |

(Continued)

FOREIGN PATENT DOCUMENTS

EP    0876808    11/1998

(Continued)

OTHER PUBLICATIONS

Mantovani, Diego, "Shape Memory Alloys:Properties and Biomedical Applications," reprinted from JOM, a Publication of The Minerals, Metals & materials Society, vol. 52, No. 10, Oct. 2000, pp. 36-44, available at http://www.tms.org/pubs/journals/JOM/jom.html.

(Continued)

*Primary Examiner*—Julian W Woo
(74) *Attorney, Agent, or Firm*—Stephen Donovan; Allergan, Inc.

(57) ABSTRACT

A fatigue-resistant inflatable gastric banding device suitable for laparoscopic placement around the stomach of a patient for the treatment of obesity and a method for such treatment are disclosed. The device includes a gastric band having a chambered inflatable member, substantially coextensive with an inner stomach facing surface of the band, that does not crease, wrinkle or fold when adjusted, so as to present a substantially smooth contour along the inner circumference, and to avoid fatigue or failure of the member itself. A gastric band having multiple inflatable compartments or chambers, which may be inflated together or individually is also disclosed.

14 Claims, 6 Drawing Sheets

U.S. PATENT DOCUMENTS

| | | | |
|---|---|---|---|
| 4,592,339 A | 6/1986 | Kuzmak et al. | |
| 4,696,288 A | 9/1987 | Kuzmak | 128/898 |
| 4,708,140 A * | 11/1987 | Baron | 606/158 |
| 5,074,868 A | 12/1991 | Kuzmak | 606/157 |
| 5,152,770 A * | 10/1992 | Bengmark et al. | 606/158 |
| 5,188,609 A | 2/1993 | Bayless et al. | |
| 5,226,429 A | 7/1993 | Kuzmak | |
| 5,391,156 A | 2/1995 | Hildwein et al. | |
| 5,449,368 A | 9/1995 | Kuzmak | |
| 5,601,604 A | 2/1997 | Vincent | |
| 5,607,418 A | 3/1997 | Arzbaecher | |
| 5,653,718 A | 8/1997 | Yoon | |
| 5,695,504 A | 12/1997 | Gifford, III et al. | |
| 5,713,911 A | 2/1998 | Racenet et al. | |
| 5,769,877 A | 6/1998 | Barreras, Sr. | |
| 5,817,113 A | 10/1998 | Gifford, III et al. | |
| 5,833,698 A | 11/1998 | Hinchliffe et al. | |
| RE36,176 E | 3/1999 | Kuzmak | |
| 5,904,697 A | 5/1999 | Gifford, III et al. | |
| 5,910,149 A | 6/1999 | Kuzmak | 606/157 |
| 5,928,195 A | 7/1999 | Malamud et al. | |
| 5,938,669 A | 8/1999 | Klaiber et al. | |
| 5,944,696 A | 8/1999 | Bayless et al. | |
| 5,944,751 A | 8/1999 | Laub | |
| 6,048,309 A | 4/2000 | Flom et al. | |
| 6,067,991 A | 5/2000 | Forsell | |
| 6,074,341 A | 6/2000 | Anderson et al. | |
| 6,102,922 A | 8/2000 | Jakobsson | 606/157 |
| 6,171,321 B1 | 1/2001 | Gifford, III et al. | |
| 6,193,734 B1 | 2/2001 | Bolduc et al. | |
| 6,203,523 B1 | 3/2001 | Haller et al. | |
| 6,210,347 B1 | 4/2001 | Forsell | |
| 6,371,965 B2 | 4/2002 | Gifford, III et al. | |
| 6,387,105 B1 | 5/2002 | Gifford, III et al. | |
| 6,419,696 B1 | 7/2002 | Ortiz et al. | |
| 6,432,040 B1 | 8/2002 | Meah | |
| 6,443,957 B1 | 9/2002 | Addis | |
| 6,443,965 B1 | 9/2002 | Gifford, III et al. | |
| 6,450,173 B1 | 9/2002 | Forsell | 128/899 |
| 6,450,946 B1 | 9/2002 | Forsell | |
| 6,451,034 B1 | 9/2002 | Gifford, III et al. | |
| 6,453,907 B1 | 9/2002 | Forsell | |
| 6,454,699 B1 | 9/2002 | Forsell | |
| 6,454,700 B1 | 9/2002 | Forsell | 600/37 |
| 6,454,701 B1 | 9/2002 | Forsell | 600/37 |
| 6,457,801 B1 | 10/2002 | Fish et al. | |
| 6,460,543 B1 | 10/2002 | Forsell | 128/898 |
| 6,461,293 B1 | 10/2002 | Forsell | |
| 6,463,935 B1 | 10/2002 | Forsell | 128/899 |
| 6,470,892 B1 | 10/2002 | Forsell | 128/899 |
| 6,475,136 B1 | 11/2002 | Forsell | 600/37 |
| 6,485,496 B1 | 11/2002 | Suyker et al. | |
| 6,491,704 B2 | 12/2002 | Gifford, III et al. | |
| 6,491,705 B2 | 12/2002 | Gifford, III et al. | |
| 6,511,490 B2 * | 1/2003 | Robert | 606/151 |
| 6,517,556 B1 | 2/2003 | Monassevitch | |
| 6,547,801 B1 | 4/2003 | Dargent et al. | |
| 6,565,582 B2 | 5/2003 | Gifford, III et al. | |
| 6,678,561 B2 | 1/2004 | Forsell | 607/40 |
| 7,017,583 B2 | 3/2006 | Forsell | 128/899 |
| 7,144,400 B2 | 12/2006 | Byrum | 606/140 |
| 7,191,007 B2 | 3/2007 | Desai | 607/33 |
| 7,311,716 B2 | 12/2007 | Byrum | 606/151 |
| 7,351,198 B2 | 4/2008 | Byrum | 600/31 |
| 7,351,240 B2 | 4/2008 | Hassler, Jr. | 604/891.1 |
| 7,353,747 B2 | 4/2008 | Swayze | 92/92 |
| 7,364,542 B2 | 4/2008 | Jambor | 600/37 |
| 7,367,937 B2 | 5/2008 | Jambor | 600/37 |
| 7,374,557 B2 | 5/2008 | Conlon | 604/175 |
| 7,374,565 B2 | 5/2008 | Hassler, Jr. | 606/151 |
| 7,390,294 B2 | 6/2008 | Hassler, Jr. | 600/37 |
| 7,416,528 B2 | 8/2008 | Crawford | 600/37 |
| 7,481,763 B2 | 1/2009 | Hassler, Jr. | 600/37 |
| 7,553,298 B2 | 6/2009 | Hunt | 604/175 |
| 7,561,916 B2 | 7/2009 | Hunt | 607/36 |
| 7,594,885 B2 | 9/2009 | Byrum | 600/37 |
| 7,599,743 B2 | 10/2009 | Hassler, Jr. | 607/61 |
| 7,599,744 B2 | 10/2009 | Giordano | 607/61 |
| 7,601,162 B2 | 10/2009 | Hassler, Jr. | 606/151 |
| 7,615,001 B2 | 11/2009 | Jambor | 600/37 |
| 7,618,365 B2 | 11/2009 | Jambor | 600/37 |
| 7,651,483 B2 | 1/2010 | Byrum | 604/288.01 |
| 7,658,196 B2 | 2/2010 | Ferreri | 128/899 |
| 2001/0011543 A1 | 8/2001 | Forsell | 128/899 |
| 2003/0045902 A1 | 3/2003 | Weadock | |
| 2003/0066536 A1 | 4/2003 | Forsell | |
| 2003/0100910 A1 | 5/2003 | Gifford, III et al. | |
| 2003/0181890 A1 | 9/2003 | Schulze et al. | |
| 2003/0208212 A1 | 11/2003 | Cigaina | |
| 2004/0133219 A1 | 7/2004 | Forsell | 606/151 |
| 2004/0254537 A1 | 12/2004 | Conlon | 604/175 |
| 2005/0070937 A1 | 3/2005 | Jambor | 606/153 |
| 2005/0131352 A1 | 6/2005 | Conlon | 604/175 |
| 2005/0143766 A1 | 6/2005 | Bachmann | 606/158 |
| 2005/0240155 A1 | 10/2005 | Conlon | 604/174 |
| 2005/0283118 A1 | 12/2005 | Uth | 604/175 |
| 2005/0283119 A1 | 12/2005 | Uth | 604/175 |
| 2005/0288739 A1 | 12/2005 | Hassler | 607/61 |
| 2005/0288740 A1 | 12/2005 | Hassler | 607/61 |
| 2006/0161186 A1 | 7/2006 | Hassler | 606/153 |
| 2006/0178647 A1 | 8/2006 | Stats | 604/288.01 |
| 2006/0189887 A1 | 8/2006 | Hassler | 600/561 |
| 2006/0189888 A1 | 8/2006 | Hassler | 600/561 |
| 2006/0199997 A1 | 9/2006 | Hassler | 600/37 |
| 2006/0211912 A1 | 9/2006 | Dlugos | 600/37 |
| 2006/0211913 A1 | 9/2006 | Dlugos | 600/37 |
| 2006/0211914 A1 | 9/2006 | Hassler | 600/37 |
| 2006/0293627 A1 | 12/2006 | Byrum | 604/175 |
| 2007/0015954 A1 | 1/2007 | Dlugos | 600/37 |
| 2007/0015955 A1 | 1/2007 | Tsonton | 600/37 |
| 2007/0027356 A1 | 2/2007 | Ortiz | 600/37 |
| 2007/0149947 A1 | 6/2007 | Byrum | 604/508 |
| 2007/0167672 A1 | 7/2007 | Dlugos | 600/37 |
| 2007/0185373 A1 | 8/2007 | Tsonton | 600/37 |
| 2007/0203313 A1 | 9/2007 | Conlon | 604/288.01 |
| 2007/0235083 A1 | 10/2007 | Dlugos | 137/223 |
| 2007/0250086 A1 | 10/2007 | Wiley | 606/157 |
| 2008/0009680 A1 | 1/2008 | Hassler | 600/300 |
| 2008/0015406 A1 | 1/2008 | Dlugos | 600/37 |
| 2008/0249806 A1 | 10/2008 | Dlugos | 705/3 |
| 2008/0250340 A1 | 10/2008 | Dlugos | 715/771 |
| 2008/0250341 A1 | 10/2008 | Dlugos | 715/771 |
| 2009/0157106 A1 | 6/2009 | Marcotte | 606/157 |
| 2009/0171378 A1 | 7/2009 | Coe | 606/157 |
| 2009/0192404 A1 | 7/2009 | Ortiz | 600/547 |
| 2009/0204131 A1 | 8/2009 | Ortiz | 606/157 |
| 2009/0204132 A1 | 8/2009 | Ortiz | 606/157 |
| 2009/0228028 A1 | 9/2009 | Coe | 606/157 |

FOREIGN PATENT DOCUMENTS

| | | |
|---|---|---|
| EP | 1488824 A1 | 12/2004 |
| EP | 1591140 A1 | 11/2005 |
| EP | 1736195 A1 | 12/2006 |
| EP | 1736198 A1 | 12/2006 |
| EP | 1543861 B1 | 3/2007 |
| EP | 1829505 A2 | 9/2007 |
| EP | 1829506 A1 | 9/2007 |
| EP | 1870126 A1 | 12/2007 |
| EP | 1736196 B1 | 8/2008 |
| EP | 1992315 A1 | 11/2008 |
| EP | 1736197 B1 | 12/2008 |
| EP | 1736199 B1 | 2/2009 |
| EP | 1736194 B1 | 3/2009 |

| | | | |
|---|---|---|---|
| EP | 1574189 B1 | 5/2009 | |
| EP | 1547643 B1 | 6/2009 | |
| EP | 1736202 B1 | 7/2009 | |
| EP | 1829504 B1 | 7/2009 | |
| EP | 1547549 B1 | 8/2009 | |
| EP | 1491168 B1 | 11/2009 | |
| EP | 1743605 B1 | 11/2009 | |
| FR | 2783153 | 3/2000 | |
| FR | 2921822 | 4/2009 | |
| GB | 1174814 | 12/1969 | |
| WO | WO00/00108 A1 | 1/2000 | |
| WO | 00/09047 A1 | 2/2000 | |
| WO | WO01/47435 | 7/2001 | |
| WO | WO02/19953 | 3/2002 | |
| WO | 2004/019671 A2 | 3/2004 | |

OTHER PUBLICATIONS

Brailovski, V., et al., "Review of Shape Memory Alloys Medical Applications in Russia," published in Bio-Medical of Materials & Engineering, vol. 6, No. 4, pp. 291-298 (1996).

Anson, Tony, "Shape Memory Alloys—Medical Applications," Source: Materials World, vol. 7, No. 12, pp. 745-747, Dec. 1999, available at http://www.azom.com/details.asp?ArticleID=134.

* cited by examiner

FATIGUE-RESISTANT GASTRIC BANDING DEVICE

CROSS REFERENCE TO RELATED APPLICATIONS

This application claims the benefit of Provisional Patent Application Ser. No. 60/407,219, filed Aug. 28, 2002 with the United States Patent Trademark Office, and which is incorporated herein by reference.

BACKGROUND OF THE INVENTION

1. Field of the Invention

The present invention relates generally to surgically implanted gastric bands for encircling the stomach having notches, ribs and/or chambers in the inflatable portion to reduce fatigue or crease fold failure in the device, while increasing the range of adjustment. A method for treating morbid obesity utilizing a fatigue-resistant gastric banding device is also disclosed.

2. Description of the Related Art

A belt-like gastric band for encircling the stomach to control morbid obesity is disclosed by Vincent in U.S. Pat. No. 5,601,604, incorporated herein by reference. The band comprises a belt that can be passed around the stomach and locked into an encircling position in order to create a stoma opening within the stomach. An adjustable portion of the band comprises an inflatable member, which permits fine adjustment of the stoma opening after the stoma is created by locking the band in place. The stoma opening may be adjusted by injecting or withdrawing a fluid into or from an inflatable member. The means for injecting the fluid into the inflatable member usually comprises a fill port located beneath the skin that can be accessed extracorporeally by transdermal injection. Thus, following implantation, the gastric band can be adjusted to enlarge or reduce the stoma as required.

The gastric band is implanted surgically, via open or laparoscopic surgery, which may involve placement of a calibrating apparatus in the stomach to position the stoma and size the pouch created above the stoma. The gastric band is imbricated in position about the stomach to prevent slippage, usually by gastro-gastric sutures (i.e. tissue is wrapped over the band and sutured to itself).

As disclosed by Vincent, the inflatable member or shell is preferably substantially coextensive with an inner stomach-facing surface of the gastric band. Furthermore, it has been observed that the inflatable member should not wrinkle or fold when adjusted, so as to present a substantially smooth contour along the inner circumference. This ensures not only that stomach tissue will not be pinched by the inflatable member, which could lead to discomfort or necrosis, but also protects the shell from a phenomenon known as crease fold failure, which may occur if it is inflated beyond its intended range of adjustment. In the field, it has been observed that silicone or other elastomeric materials commonly used in the manufacture of gastric bands can fatigue or fail if repeatedly compressed, folded, wrinkled, buckled under stress or creased by, for example, over-inflation. This failure mode, which may include abrasion of the opposing surfaces against one another, abrasion of the inner surface of the fold "peak" against the opposing chamber wall, or fatigue of the material at folder intersections (the most highly-stressed areas), is sometimes referred to as crease fold failure.

In some cases, it has also been noted that existing adjustable gastric bands do not provide the overall size or range of adjustment desirable for use in particular patients. For instance, existing gastric bands may be either too large or too small to encircle a patient's stomach, while still allowing for a properly sized stoma. This may be due, for instance, to variations from patient to patient and their individual internal physiologies. Thus, gastric bands are now available in several different sizes, measured according to the circumference of the band (e.g. 9.75 cm, 11 cm, etc.). But due to variations in not only patient physiology, but also in the location and encircling position of the band, the surgical technique used, etc., it may not be evident what size band is necessary until a patient is undergoing surgery. Rather than have a variety of different sizes of gastric bands on hand during the surgical procedure, it would be desirable to have one universal size gastric band available that is adjustable over a wider range than those bands known in the prior art.

If the overall size of the gastric band is increased, the inflatable shell portion may not be capable of being adjusted to form a relatively small stoma without creases, wrinkles or folds forming on the inner stomach-facing surface, which may lead to fatigue or failure of the inflatable member, necessitating additional surgery. It would therefore be desirable to provide a universal size of a fatigue-resistant gastric band having an inflatable member that can be adjusted over a wide range of stoma openings.

OBJECTS OF THE INVENTION

The foregoing demonstrates a need for a surgically implantable gastric band having a universal size and offering a range of adjustability suitable for use in a variety of patients.

It is therefore an object of the present invention to provide a gastric band universally sized for use in patients with varying internal physiologies.

It is another object of the present invention to provide a gastric band having an inflatable member adjustable over a wider range of stoma openings than currently available devices.

It is yet another object of the invention to provide a gastric band having an inflatable member that is substantially coextensive with an inner stomach-facing surface of the gastric band.

Still another object of the present invention is to provide a gastric band having an inflatable member that does not wrinkle or fold when adjusted over a wide range, so as to present a substantially smooth contour along the inner circumference, and to avoid fatigue or failure of the member itself.

Various other objects, advantages and features of the present invention will become readily apparent from the ensuing detailed description and the novel features will be particularly pointed out in the appended claims.

SUMMARY OF THE INVENTION

A preferred embodiment of the invention provides a fatigue-resistant gastric banding device for the treatment of morbid obesity. The device has a gastric band suited for laparoscopic placement around the stomach of a patient to form an adjustable stoma opening. The gastric band has a multi-chambered inflatable member for adjusting the inner circumference of the band. The inflatable member is preferably substantially coextensive with an inner stomach-facing surface of the gastric band. The inflatable member is chambered so as to not wrinkle or fold when adjusted over its range of adjustment, thereby presenting a substantially smooth contour along the inner circumference and reducing fatigue or failure of the device.

Another embodiment of the present invention is a gastric band having an inflatable shell including a plurality of chambers. Separating the chambers is at least one notch and/or reinforcing rib. Upon inflation of the gastric band, the chambers ribs and/or notches eliminate creasing, folding or wrinkling of said inflatable shell, thereby reducing fatigue on the device.

Yet another embodiment of the present invention is a method of treating morbid obesity. The method of treatment includes the steps of providing a gastric band having an inflatable shell with a plurality of chambers, ribs and/or notches. A further step requires placing the gastric band around the stomach of a patient to be treated for morbid obesity; and inflating the gastric band to form a stoma.

The fatigue-resistant gastric band of the present invention may be adjusted by adding fluid to or removing fluid from the chambered inflatable member or shell by means of a subcutaneous access port, via a remotely controllable pump, using pressurized fluid or through other means well known to one skilled in the art.

BRIEF DESCRIPTION OF THE DRAWINGS

The following detailed description given by way of example, but not intended to limit the invention solely to the specific embodiments described, may best be understood in conjunction with the accompanying drawings in which.

DETAILED DESCRIPTION OF CERTAIN PREFERRED EMBODIMENTS

Figure 1:
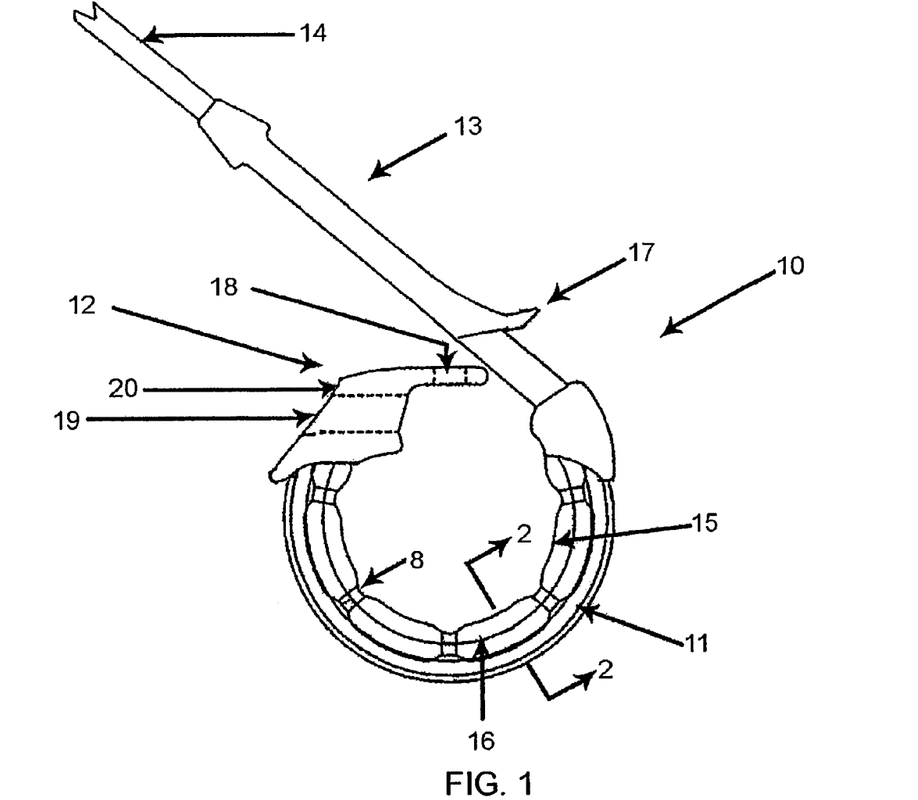
FIG. 1 is a top view of a gastric band according to one embodiment of the present invention.

An inflatable gastric band 10 according to the present invention is shown in FIG. 1. The gastric band 10 has a body portion 11 and an inflatable portion or shell 16. The body portion 11 has a head end 12 and a tail end 13. The head end 12 of the body portion 11 has a buckle 19 with a pull-tab 18. The tail end 13 includes a belt tab 17. Upon insertion of the tail end 13 including a fill tube 14 through the buckle 19, the tail end 13 is drawn through the buckle 19 until the belt tab 17 catches on the exit side 20. In this position the gastric band 10 is releasably locked in a closed loop position and secured by the buckle 19 and the belt tab 17.

The fill tube 14, which is generally a tube having a single lumen (not shown) coextensive therewith, is connected to an end of the gastric band 10. In FIG. 1 it is shown attached to the tail end 13 and in fluid communication with an inflatable shell 16. It will be apparent to one of skill in the art that other arrangements of the fill tube 14 could be made including attachment to the head end 12 without departing from the scope of the present invention.

Figure 2:
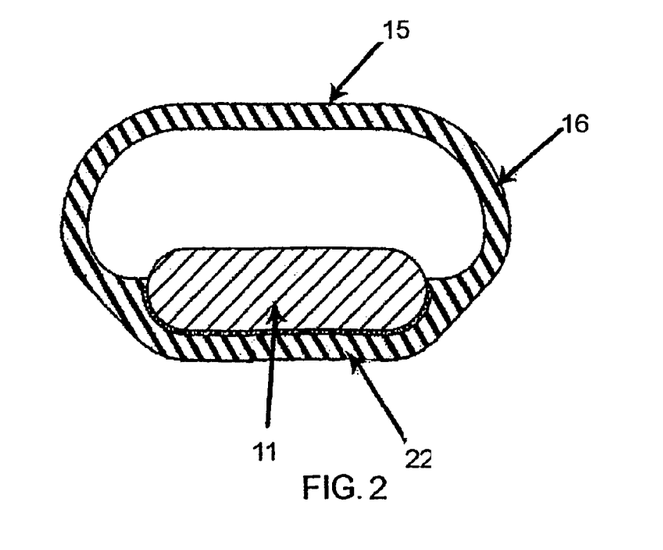
FIG. 2 is a cross-sectional view of the gastric band shown in FIG. 1 taken along line 2-2.

The inflatable shell 16 is formed to receive the body portion 11 as shown in FIG. 2, which is a cross sectional view of FIG. 1 taken along line 2-2. The inflatable shell 16 is preferably substantially coextensive with the body portion 11, as shown in FIG. 1. The body portion 11 may be attached to the interior of the inflatable shell 16 through the use of adhesives compatible for use within the body or other methods known to those skilled in the art of implantable medical device manufacture. The inflatable shell 16 includes an inner stomach-facing surface 15 that forms a stoma when placed around the stomach. It is this surface that has traditionally been the location of failure due to crease fold fatigue.

Figure 3:
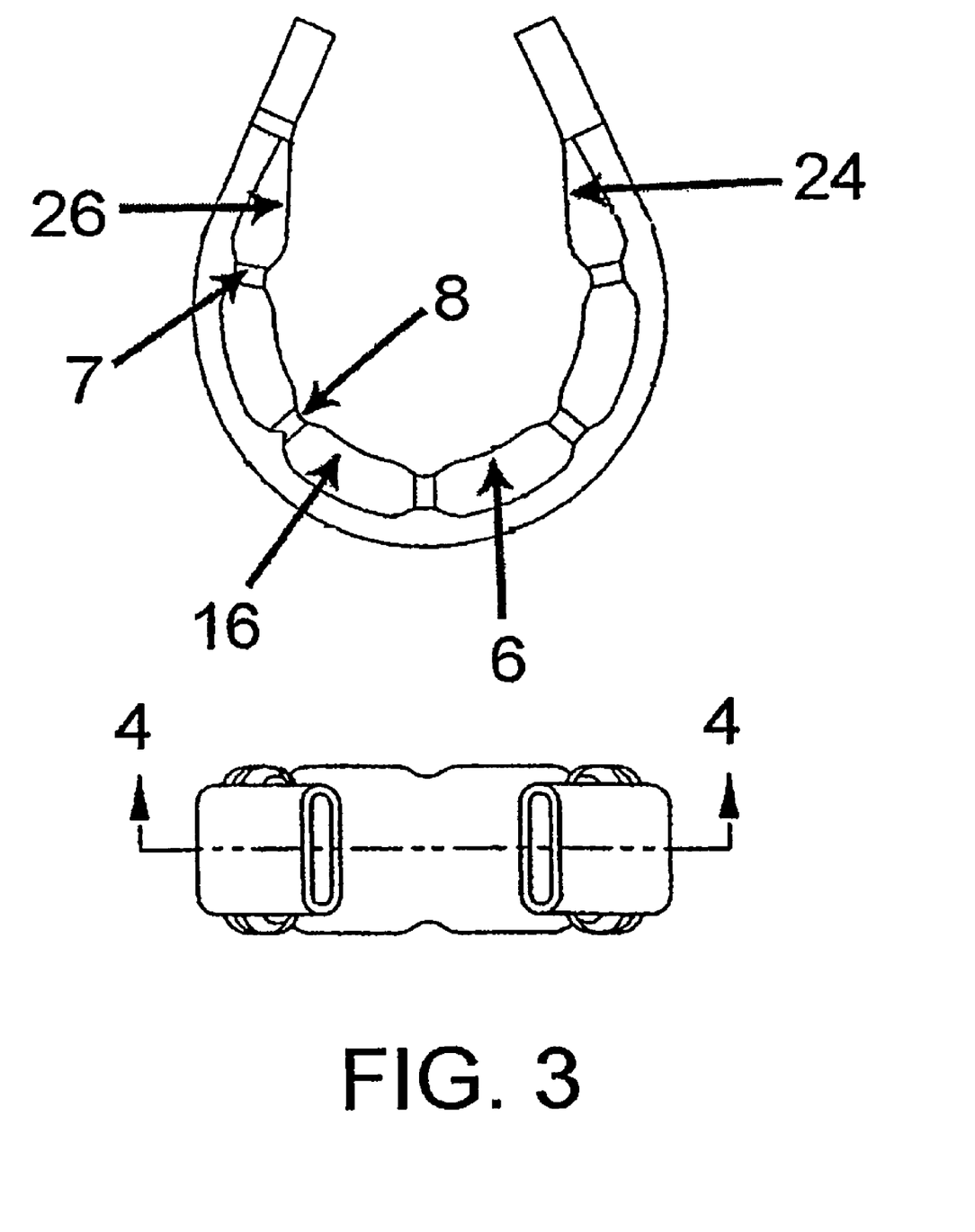
FIG. 3 is a top and side view of the encircling portion of fatigue-resistant inflatable shell of the gastric band of FIG. 1.

To reduce the potential for crease fold failure or high stresses in the inner surface 15, the inflatable shell 16 has pre-formed stress-reducing notches 8 separating chambers 6. FIG. 3 shows a top view of the inflatable shell 16 of gastric band 10 with plurality of chambers 6 each separated by a respective notch 8. FIG. 3 differs from FIG. 1 in that it shows just the inflatable shell 16 without the inner portion 11 of the gastric band 10.

Figure 4:
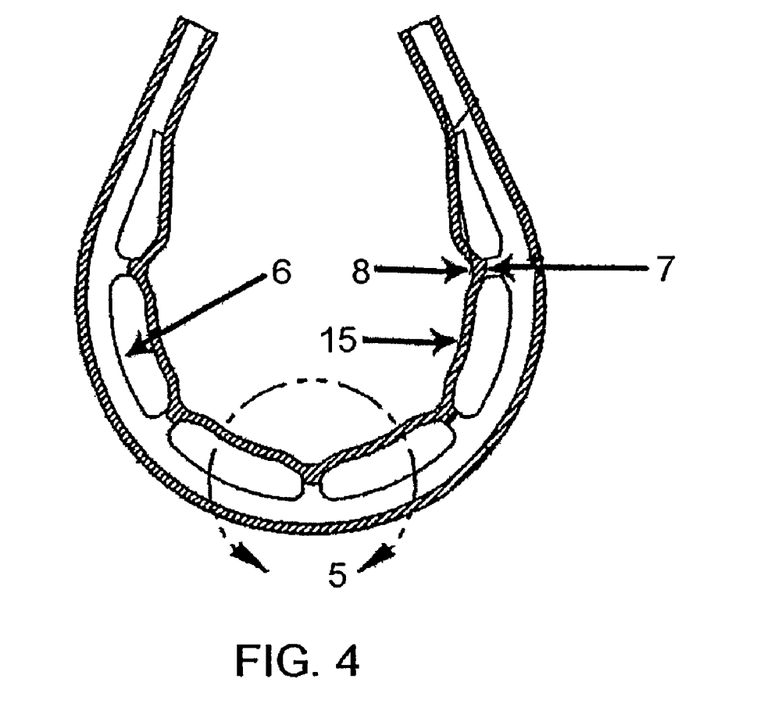
FIG. 4 is a cross-sectional top view of the fatigue-resistant inflatable shell of FIG. 3 taken along line 4-4.

Similarly, FIG. 4 shows a cross-sectional top view of the inflatable shell 16 shown in FIG. 3. In FIG. 4, the inside of the inflatable shell 16 is depicted with reinforcing ribs 7 at each of the notches 8 separating each of the chambers 6. However, as shown in FIG. 3 the first chamber 24 and last chamber 26 of the inflatable shell 16 may be formed with only one rib 7.

The band may be formed with a single notch 8 along the inner stomach-facing surface 15 of the inflatable shell 16, or more preferably, with multiple notches 8. Similarly, the band may be formed with a single reinforcing rib 7 inside the inflatable shell 16, or more preferably, with multiple ribs 7. Most preferably, the inflatable shell 16 is formed with corresponding ribs 7 and notches 8. The notches 8, chambers 6, and ribs 7 are formed in the inflatable shell 16 during the manufacturing process and are a feature of the inflatable shell 16 of the gastric band 10 whether filled or unfilled (i.e. whether the band is inflated or un-inflated). This helps to ensure that upon initial positioning of the gastric band 10 there is no pinching of the stomach.

Figure 6:
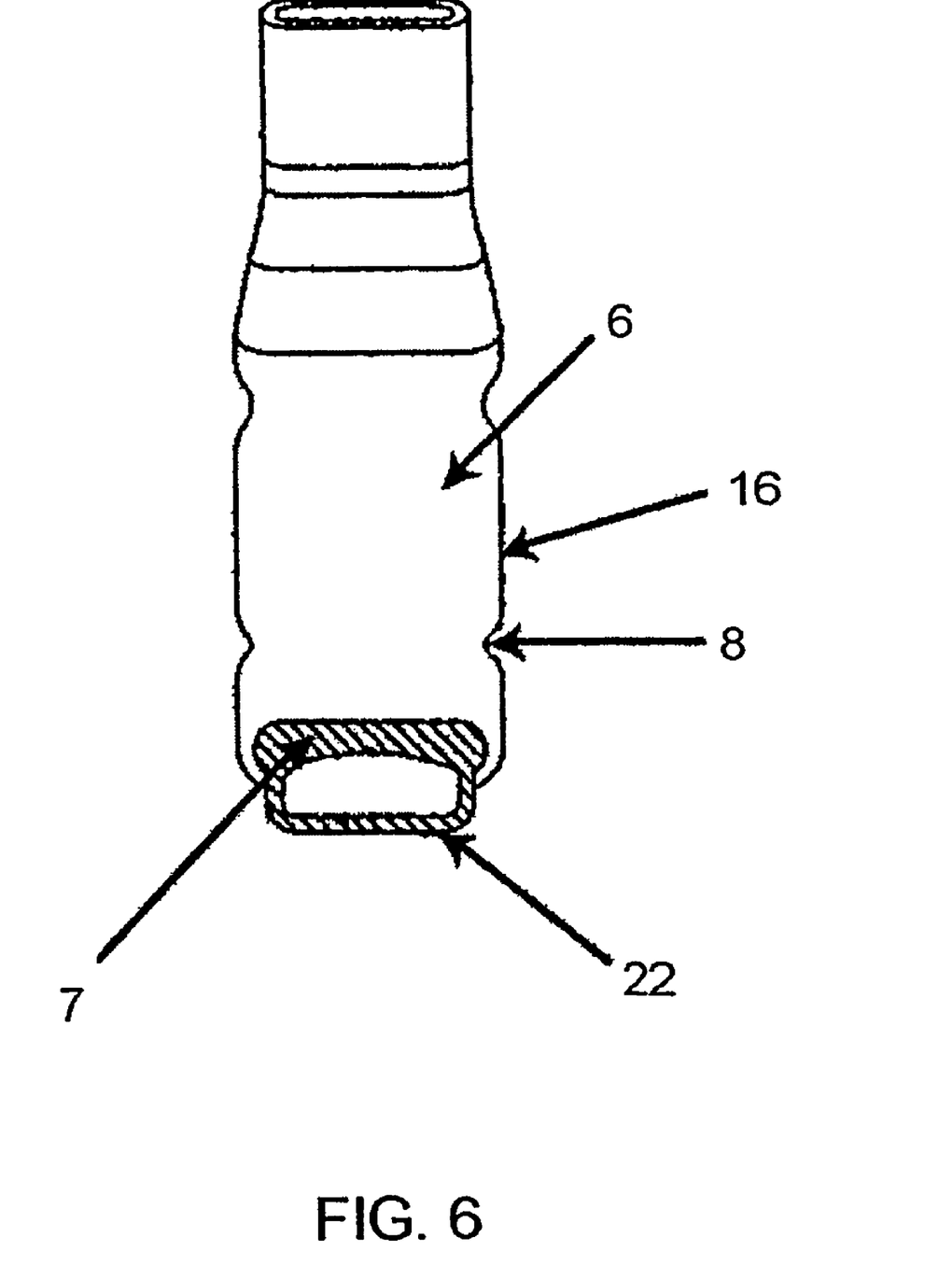
FIG. 6 is a cross-sectional view of the fatigue-resistant inflatable shell of FIG. 3 taken along line 6-6 showing the relative thickness of a reinforcing rib.
Figure 7:
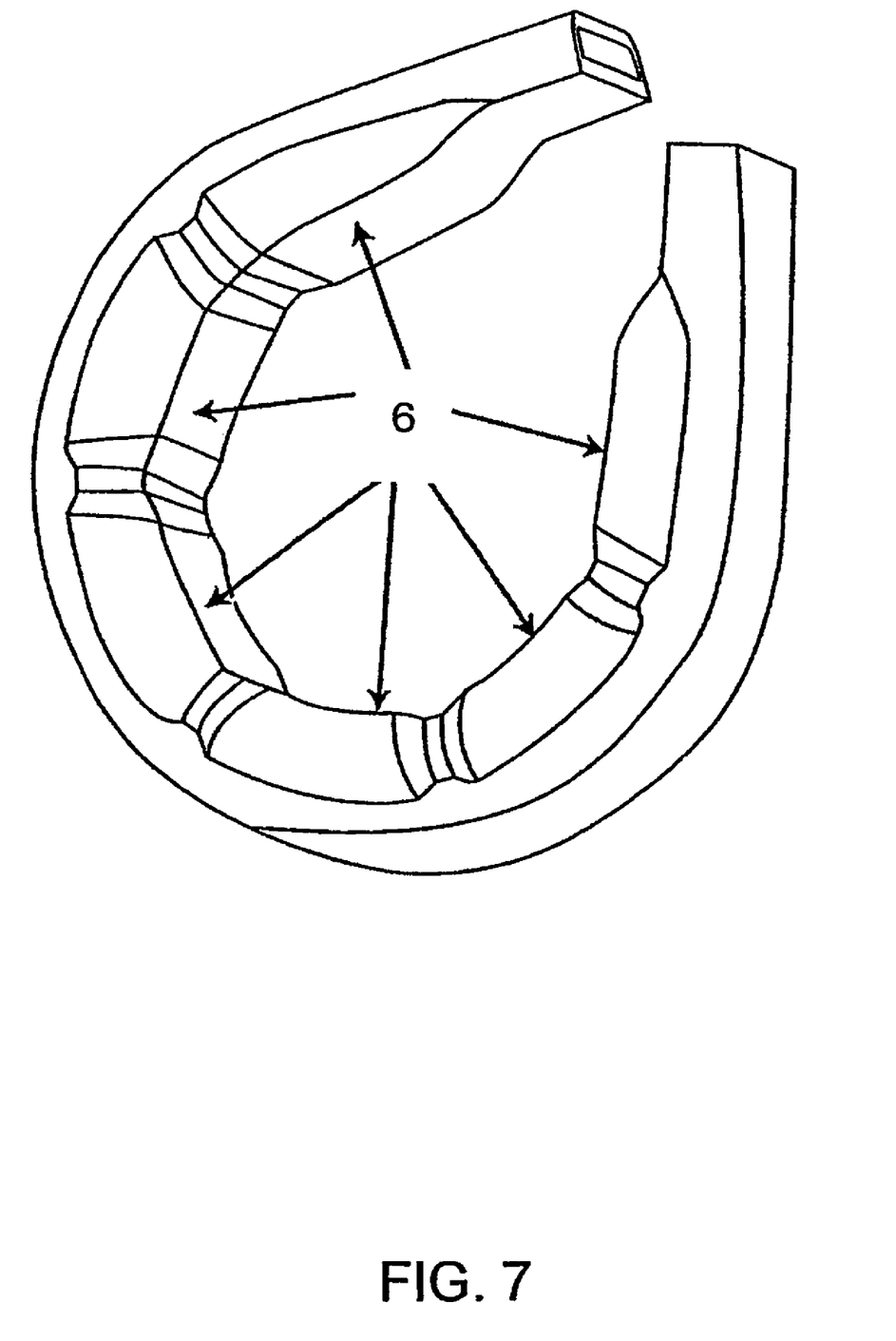
FIG. 7 is a perspective view of the encircling portion of a fatigue-resistant inflatable shell of a gastric band according to the present invention.
Figure 8:
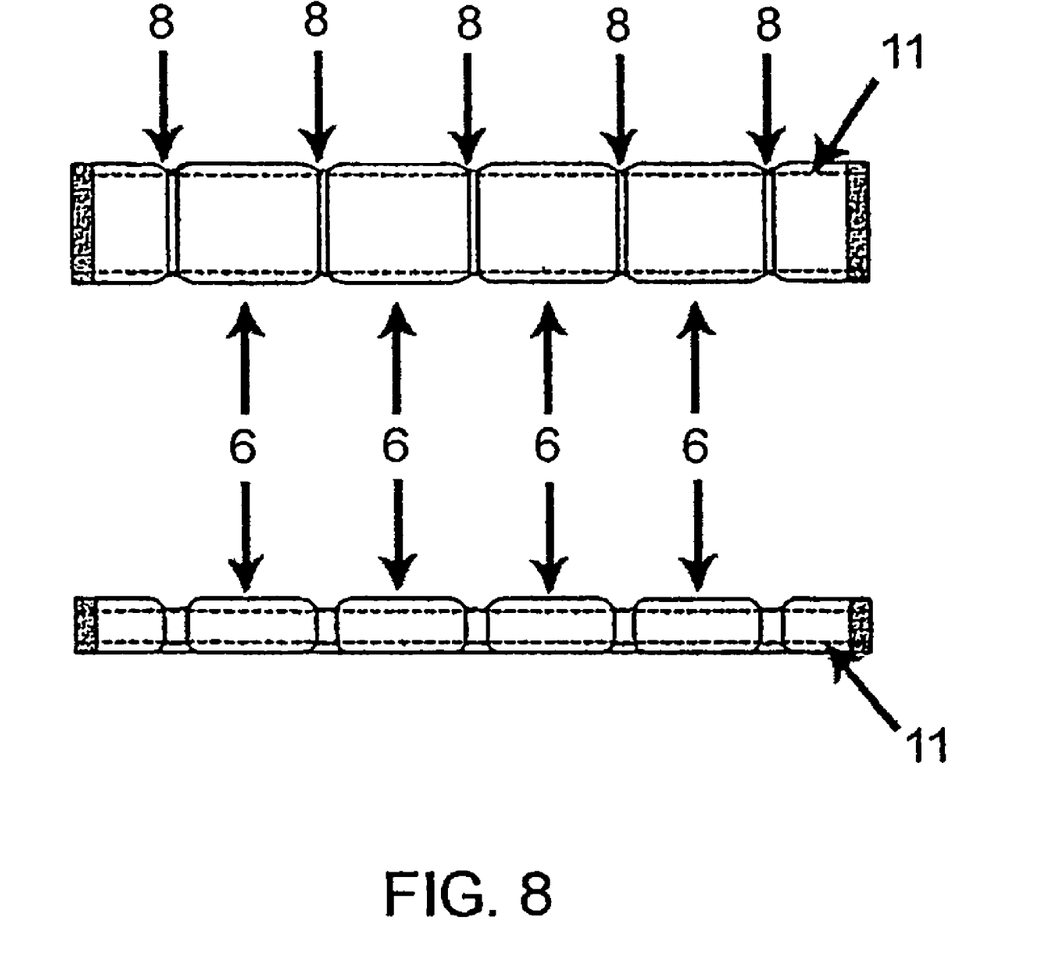
FIG. 8 is a top and side view of a portion of the gastric band of FIG. 1 straightened to show the width and projection of the chambers in relation to the inner band portion.

FIG. 6 shows a cross sectional view of the inflatable shell 16 of FIG. 3 taken along line 6-6 In FIG. 6 the thickness of the rib 7 can be seen relative to the thickness the inflatable shell 16. FIG. 6 also shows that the width of the chambers 6 may extend beyond the width of an outer surface 22 of the inflatable shell 16. Similarly, FIG. 8 shows the chambers 6 extending beyond the width of the body portion 11 (designated by the dotted line). The greater size of the chambers 6 relative to the body portion 11 helps to evenly distribute the forces applied to the stomach through the inflation of the gastric band 10.

Figure 5:
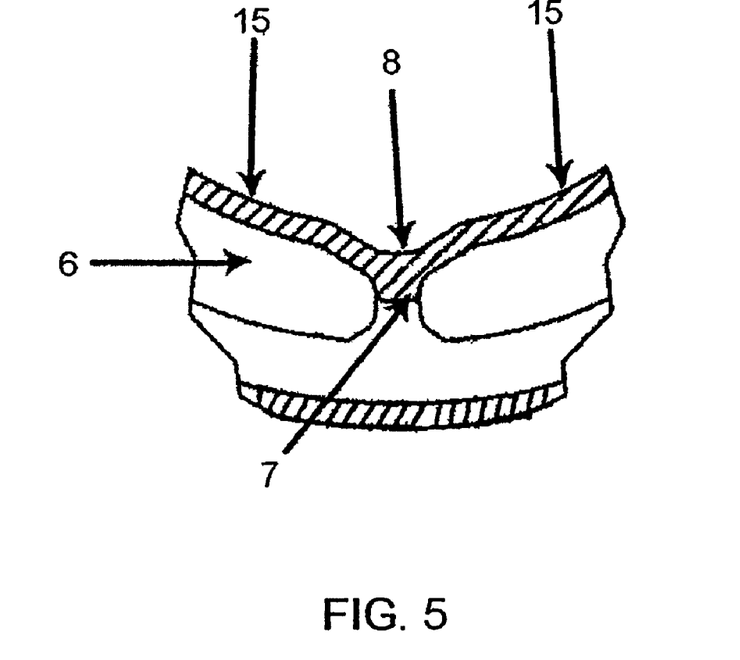
FIG. 5 is a close up cross-sectional view of a convolution point of the fatigue-resistant inflatable shell of FIG. 4 taken in area 5.

FIG. 5 shows a close-up view of a notch 8 and rib 7 of the inflatable shell 16. Also shown in FIG. 5 are chambers 6 on either side of the rib 7. From FIG. 5 it can be seen that the portions of the inner surface 15 immediately adjacent to the notches 8 will not come in contact with one another upon inflation of a gastric band 10 having a inflatable shell 16 so designed. This prevents wear and rubbing of the inner surface 15. Also as a result of the notch 8, a crease will not form in the inner surface 15 of the inflatable shell 16. Further, because of this the chamber 6 can be inflated to a much greater volume forming a smaller stoma than similar sized gastric bands known in the prior art.

The effects of the notch 8 can be described as follows: the notch 8 acts as a pre-formed crease in the inflatable shell 16.

The notch 8 acts similarly to the crease that may form in gastric bands known in the prior art as it provides a point around which the body portion 11 is allowed to bend the inner surface 15 of the gastric band 10 to form a substantially circular band. One with basic geometry skills will understand that the inner surface 15 and the body portion 11 have substantially similar lengths. As a result of this, if the body portion 11 and inflatable shell 16 are not pre-formed in a circle, when they are subsequently bent into a circular form, the interior surface 15 must in some fashion eliminate a portion of its overall length to form a circle having a smaller inner circumference than outer circumference. This reduction in circumference has heretofore occurred in prior art gastric bands through the formation of undesirable creases on the inner stomach-facing surface of the gastric band, resulting in a reduced range of inflation for such bands. The formation of these creases alleviates the material stresses in forming the circular shape, but causes point loading at the top and bottom of the creases as well as providing a point of friction between two facing sides of the crease. By forming the inflatable shell 16 in a circle with pre-formed notches 8, the aforementioned stresses are drastically reduced because the notch 8, alone or in combination with a rib 7, is formed in a fashion that prevents opposing sides of the notch 8 from buckling and reduces stress, while allowing for a great range of inflation versus prior art devices. Additionally, the effects of the point loading associated with the extremities of the crease can be alleviated by the notch 8, especially when the notch 8 is formed in conjunction with a reinforcing rib 7.

In practice, the gastric band is placed in an encircling position around the stomach using known surgical techniques, including, preferably laparoscopy. Laparoscopic placement is accomplished by introducing the fill tube 14 through a laparoscopic cannula (not shown) into the patient's abdomen. Laparoscopic placement begins with blunt dissection behind the stomach, usually two to three centimeters below the gastro-esophageal junction. Typically, the end of the fill tube 14 and tail end 13 are passed around the stomach and drawn through the buckle 19, past the exit side 20 so that the belt tab 17 and buckle 19 are releasably locked together. In this sense, the band is a "one-size-fits-all" device—like that described by Vincent—but because of its notched design, the gastric band is adjustable over a greater range without creasing or folding than Vincent and other known prior art bands.

The stoma—the narrow opening in the stomach created by the band—may be adjusted after the band is secured in this single position. Prior art gastric bands employ an adjustable balloon portion that is used for post-operative adjustment of the stoma as necessary. These adjustable balloons, as discussed above, are prone to creasing. The pre-formed notches 8, chambers 6 and ribs 7 of the inflatable gastric band 10 described herein provide for increased fill volumes, e.g. up to 10 cc, without wrinkles or folds forming the shell. As in the Vincent band, the inflatable shell 16 is preferably coextensive with the inner stomach-facing surface 15 of the band between the belt tab 17 and buckle 19. The interior of the inflatable shell 16 is in fluid communication with an injection reservoir, remote pump, pressure reservoir or other adjustment means (not shown) via fill tube 14, as with prior art adjustable gastric bands. The inflatable shell 16 is gradually inflated with saline or other biocompatible fluid via the adjustment means such that the inflatable shell 16, and in particular the inner surface 15 thereof presses on and constricts the stomach underlying the band. This results in a decrease of the opening (stoma) inside the stomach directly under the encircling gastric band 10.

During inflation of the gastric band 10, the notches 8 and the ribs 7 resist deflection. At the same time, the chambers 6 do not comparatively resist deflection. This results in the areas of the inflatable shell 16 where the ribs 7 are located forming deeper notches 8 upon inflation. Accordingly, these notches 8 reduce the stresses in the inflatable shell 16 and reduce the potential for crease fold failure by eliminating contact between the two sides of the notch 8.

Despite the addition of the notches 8 and ribs 7, the gastric band 10 forms a substantially circular constriction around the stomach upon inflation. The chambers 6 of the inflatable shell 16 direct the locations of inflation. Because of the greater deflections of the inflatable shell 16 in the chambers 6 as compared to the area of the notches 8 and ribs 7, the gastric band 10, and in particular the inner surface 15 is prevented from pinching the surface of the stomach between two chamber 6 when in its inflated state, thereby reducing the potential for patient discomfort and necrosis.

The gastric band 10, as shown in FIG. 1, allows for greater adjustability and fill volume range than current gastric bands, while reducing the potential for fatigue failure, crease fold failure, or pinching of the stomach. Through the use of the chambers 6, notches 8, and the elimination of crease points, the inflatable shell 16 is provided a greater expandable range and is able to produce a smaller opening without fear of pinching the stomach. Similarly, because the crease points are eliminated, the likelihood of crease fold failure is also reduced. It is the possibility of pinching the stomach, and the potential for crease-fold failure that limit the operable range of currently known devices. The reduction of these possibilities increases the range of the stoma opening that may be formed with a single gastric band, while safely treating the obese patient.

Another embodiment of the present invention is an inflatable gastric band with an inflatable shell that is separated into multiple, isolated inflatable compartments of chambers. The inflation of the isolated chambers may or may not be circular, but will not crease, wrinkle or fold. Each isolated chamber may be inflated separately or simultaneously with other isolated chambers and will expand without creasing, wrinkling or folding. A compartmentalized gastric band allows for even greater adjustability and fill volume ranges than current gastric bands while reducing the potential for fatigue failure or crease fold failure.

For example, it may be desirable to reduce the size of the stoma in a particular direction. In such instances, a chamber on that side of the gastric band could be inflated without changing the size of the remaining chambers. Accordingly, greater flexibility is available in a device having isolated chambers that may be independently filled and adjusted. Such an arrangement requires independent filling pathways for each chamber.

The design of the present invention has been described for use in gastric banding devices, but may also be incorporated into any inflatable or expandable device that uses silicone or other elastomeric or polymeric materials where there may be a concern over crease fold failure.

Although the invention has been particularly shown and described with reference to certain preferred embodiments, it will be readily appreciated by those of ordinary skill in the art that various changes and modifications may be made therein, without departing from the spirit and scope of the invention. It is intended that the claims be interpreted as including the foregoing as well as various other such changes and modifications.

The invention claimed is:

1. A gastric band comprising:
a body portion having a width and a length sufficient to encircle a human stomach to form a stoma; and
an inflatable member coextensive with the width and continuous along the length of said body portion and having a substantially circular stomach-facing surface when the band is placed around the stomach, the inflatable member including a plurality of notches defining a plurality of chambers, the notches being structured to eliminate creasing, folding or wrinkling along the stomach-facing surface thereby reducing fatigue on the inflatable member, the body portion being located in an interior of the inflatable member.

2. The gastric band of claim 1, wherein said chambers are in fluid communication with one another.

3. The gastric band of claim 2, wherein said chambers are further defined by at least one rib of said inflatable member.

4. The gastric band of claim 1, wherein said chambers are in fluid communication with one another and are further defined by at least one rib of said inflatable member.

5. The gastric band of claim 1, wherein said chambers are in fluid isolation from one another.

6. The gastric band of claim 1, wherein the body portion is attached to an interior surface of the inflatable member.

7. The gastric band of claim 1, wherein the chambers extend beyond the width of the body portion.

8. A gastric band comprising:
an elongated body portion having connectable ends and having a width and a length sufficient to encircle a human stomach to form a stoma; and
an inflatable shell attached to said body portion and coextensive with the width and continuous along the length of said body portion, the shell forming a circular stomach-facing surface when the ends of the body portion are connected, the inflatable shell including a plurality of notches defining said plurality of chambers in fluid communication with one another;
the body portion being received in an interior of the inflatable shell.

9. The gastric band of claim 8, wherein the body portion attaches to an interior wall of the inflatable shell.

10. The gastric band of claim 8 further comprising a fill tube for inflation of said inflatable shell.

11. The gastric band of claim 8 further comprising a buckle for receiving a portion of said body portion to secure said gastric band in a circle.

12. The gastric band of claim 11, wherein gastric band is releasable secured.

13. The gastric band of claim 8, wherein said chambers are further defined by at least one rib of said inflatable shell.

14. The gastric band of claim 8, wherein the chambers extend beyond the width of the body portion.

* * * * *

UNITED STATES PATENT AND TRADEMARK OFFICE
CERTIFICATE OF CORRECTION

| | | |
|---|---|---|
| PATENT NO. | : 7,811,298 B2 | Page 1 of 1 |
| APPLICATION NO. | : 10/492784 | |
| DATED | : October 12, 2010 | |
| INVENTOR(S) | : Janel Birk | |

It is certified that error appears in the above-identified patent and that said Letters Patent is hereby corrected as shown below:

In column 3, line 32, delete "of" and insert -- of a --, therefor.

In column 4, line 44, delete "6-6" and insert -- 6-6. --, therefor.

In column 4, line 45, delete "the" and insert -- of the --, therefor.

In column 5, line 54, delete "the" and insert -- in the --, therefor.

In column 6, line 17-18, delete "chamber" and insert -- chambers --, therefor.

In column 6, line 37, delete "of" and insert -- or --, therefor.

In column 7, line 7, in claim 1, delete "the" and insert -- said --, therefor.

In column 7, line 12, in claim 1, delete "surface" and insert -- surface, --, therefor.

Signed and Sealed this
Twelfth Day of April, 2011

David J. Kappos
*Director of the United States Patent and Trademark Office*